(12) United States Patent  (10) Patent No.: US 8,296,886 B2
Vestergaard  (45) Date of Patent: Oct. 30, 2012

(54) ADJUSTABLE SUPPORT

(75) Inventor: Michael Vestergaard, Støvring (DK)

(73) Assignee: Vermund Larsen A/S, Aalborg SV (DK)

( * ) Notice: Subject to any disclaimer, the term of this patent is extended or adjusted under 35 U.S.C. 154(b) by 0 days.

(21) Appl. No.: 13/384,385

(22) PCT Filed: Jun. 29, 2010

(86) PCT No.: PCT/DK2010/050172
§ 371 (c)(1),
(2), (4) Date: Mar. 29, 2010

(87) PCT Pub. No.: WO2011/006502
PCT Pub. Date: Jan. 20, 2011

(65) Prior Publication Data
US 2012/0174318 A1 Jul. 12, 2012

(30) Foreign Application Priority Data
Jul. 16, 2009 (DK) .................................. 2009 00872

(51) Int. Cl.
A61G 13/12 (2006.01)
(52) U.S. Cl. .............................................. 5/621; 5/622
(58) Field of Classification Search .............. 5/621–624, 5/636; 248/276.1, 278.1
See application file for complete search history.

(56) References Cited

U.S. PATENT DOCUMENTS

| 2,510,198 | A | * | 6/1950 | Tesmer | 248/229.25 |
|---|---|---|---|---|---|
| 4,700,691 | A | * | 10/1987 | Tari et al. | 5/622 |
| 6,338,738 | B1 | | 1/2002 | Bellotti | |
| 6,758,808 | B2 | | 7/2004 | Paul | |
| 7,479,104 | B2 | | 1/2009 | Lau | |
| 7,665,698 | B2 | | 2/2010 | Desorbo | |
| 7,773,371 | B2 | | 8/2010 | Hillman | |

FOREIGN PATENT DOCUMENTS

| EP | 2039271 | 3/2009 |
|---|---|---|
| WO | 9315668 | 2/1992 |
| WO | 2005028943 | 3/2005 |

* cited by examiner

Primary Examiner — Fredrick Conley
(74) Attorney, Agent, or Firm — James Creighton Wray

(57) ABSTRACT

An adjustable support in the form of a headrest comprises a flexible arm (2) carrying a bifurcated branches (3a). The arm (82) is made up of identical segments (20) that can pivot in relation to each other. A wire (5) holds the arm (2) together and may be loosened by an adjusting mechanism (6) controlled by a knob (9). Partially cylindric surfaces (27, 29) on opposing ends (21, 22) of segments (20) have teeth-like projections extending transversely of the partially cylindric faces (27, 29) for mutual engagement and securing mutual position of adjacent segments (20). The adjustable support is thus able to carry greater loads than prior art adjustable supports.

12 Claims, 4 Drawing Sheets

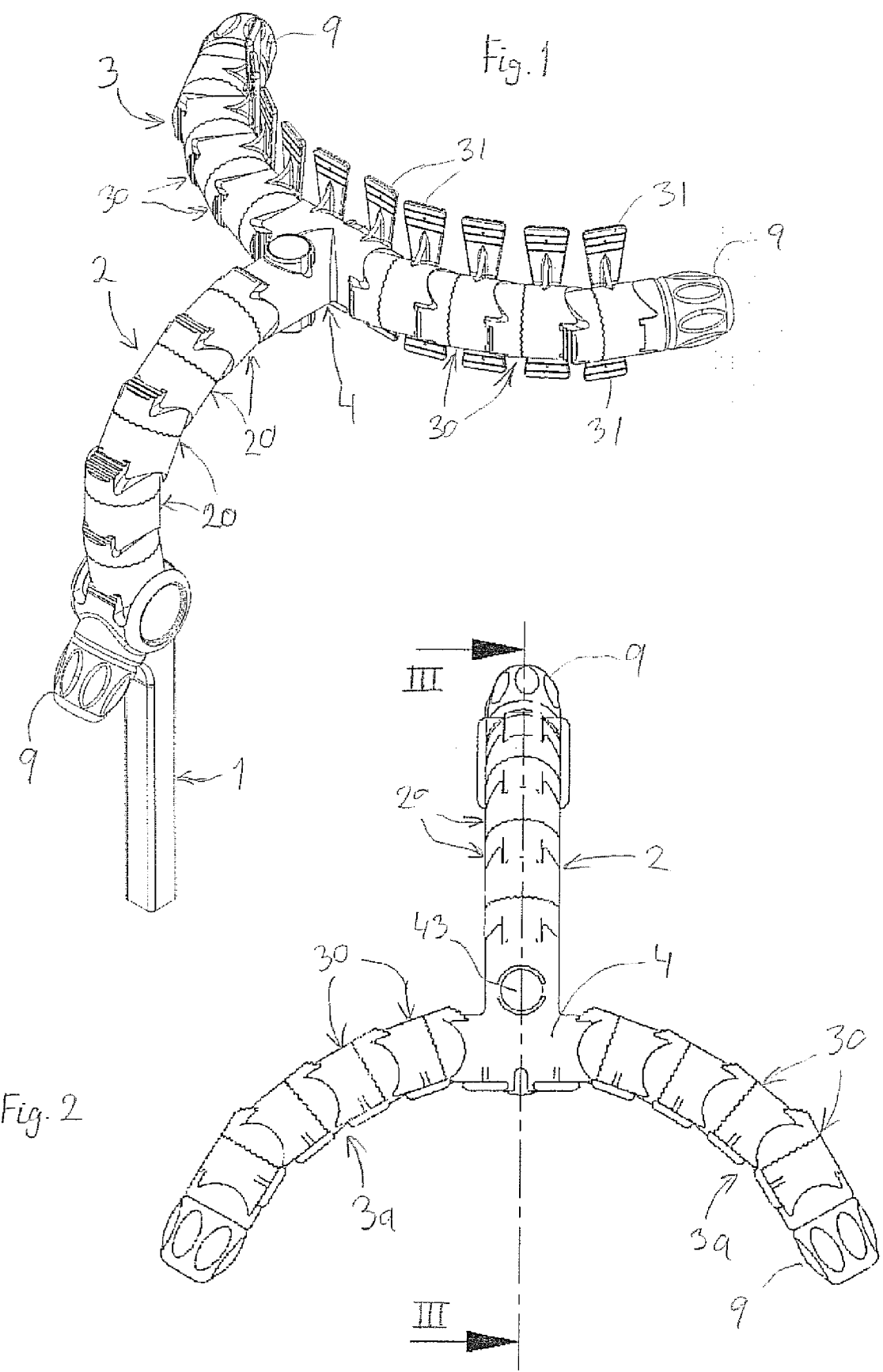

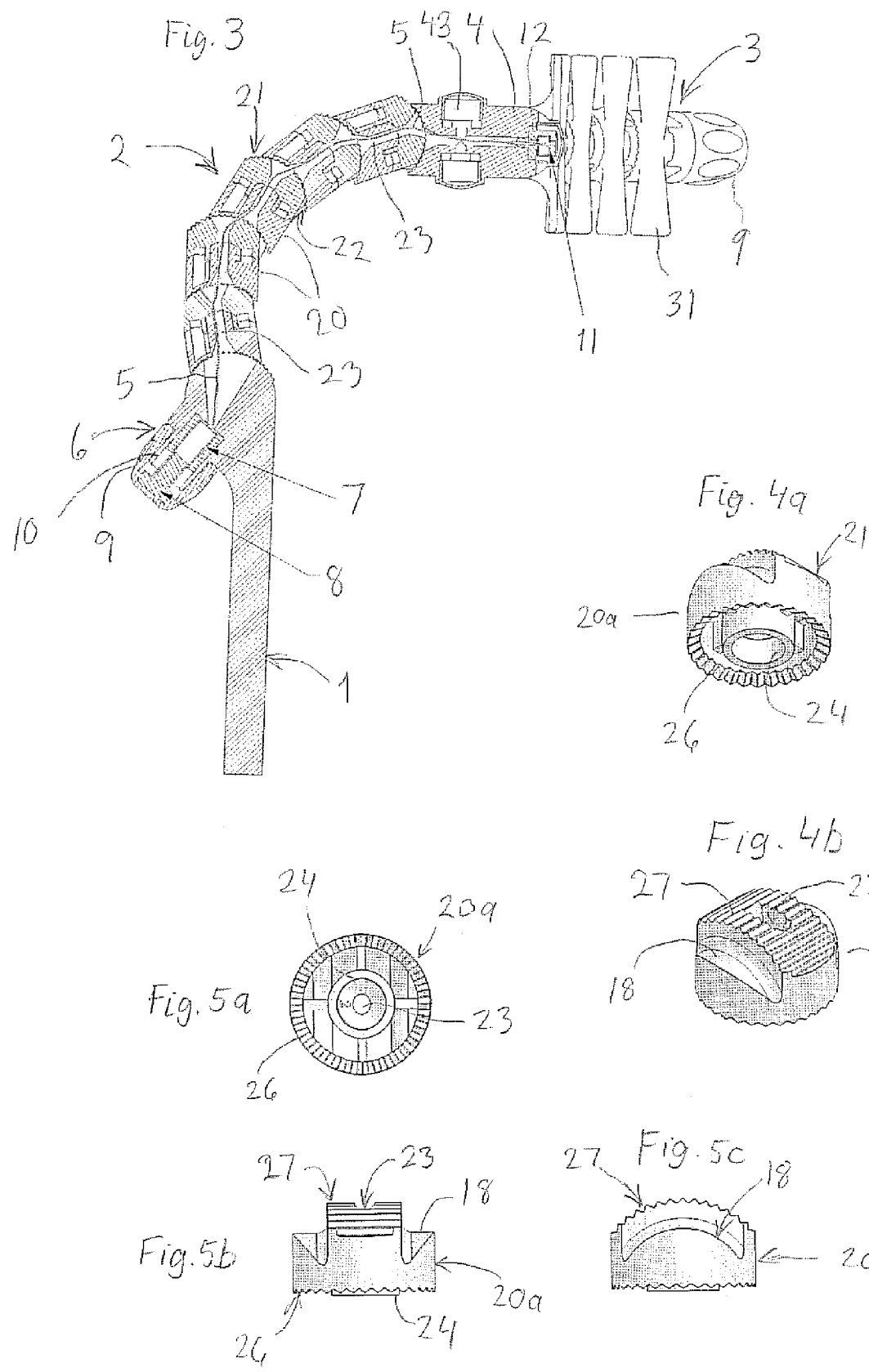

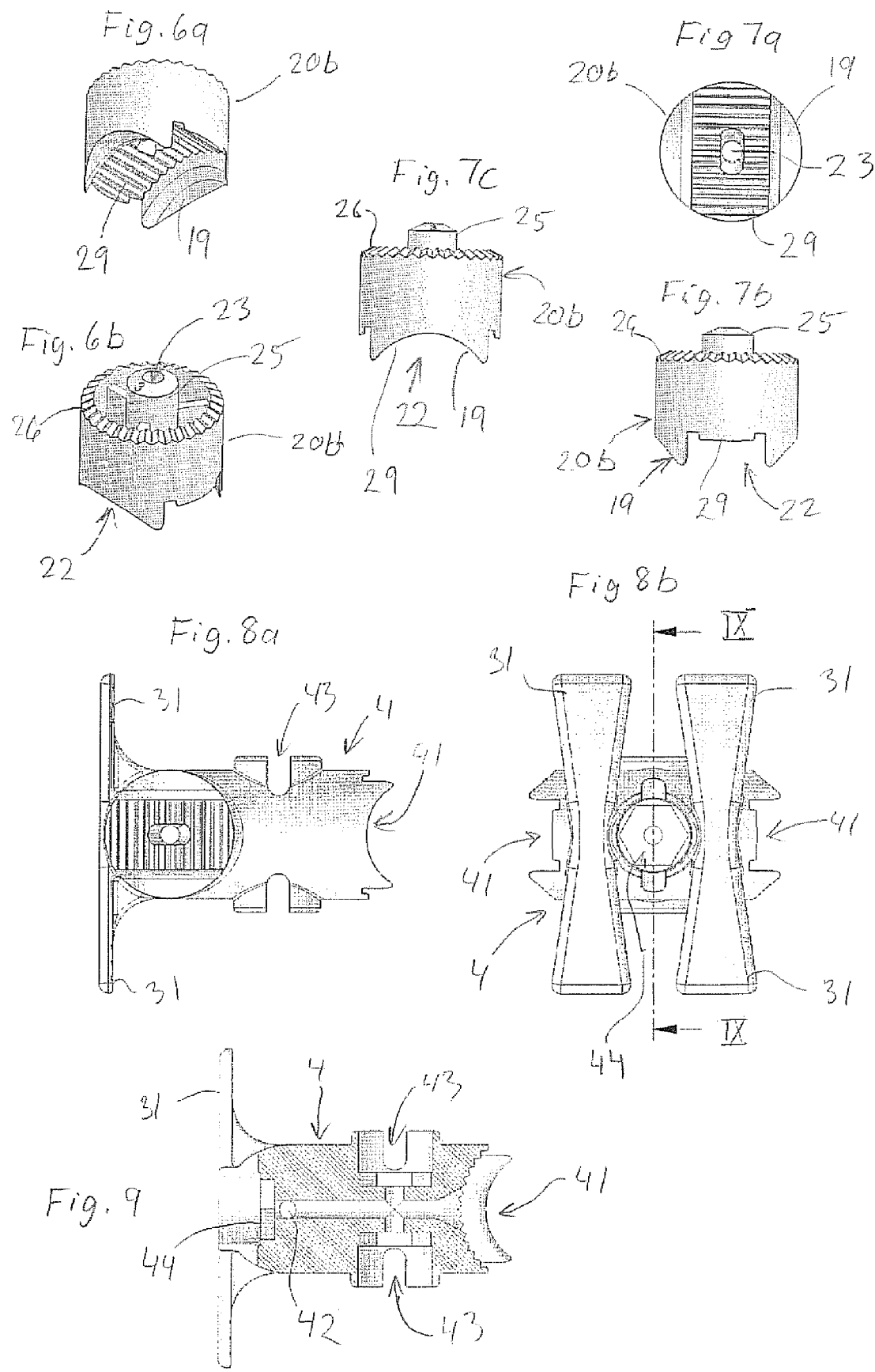

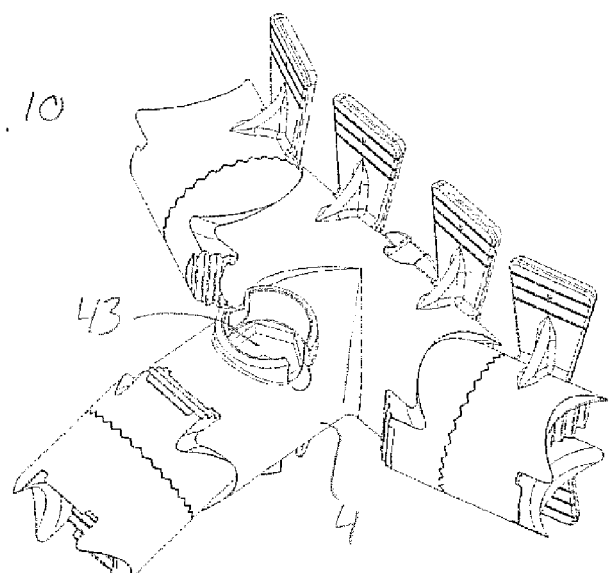
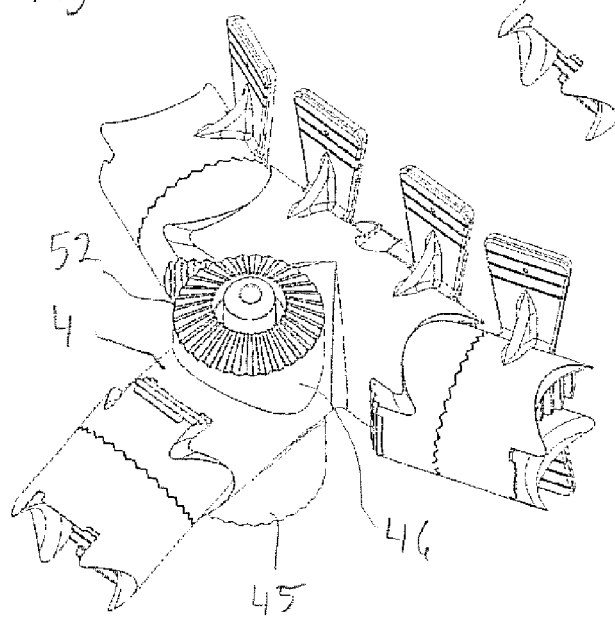
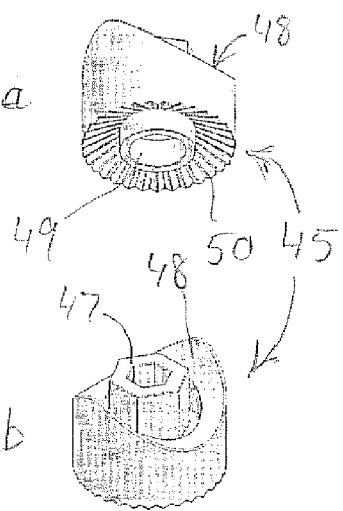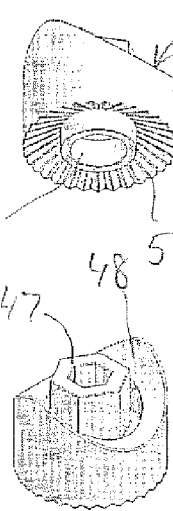
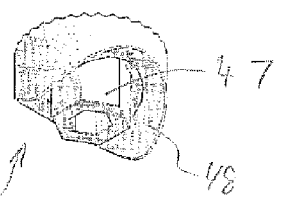
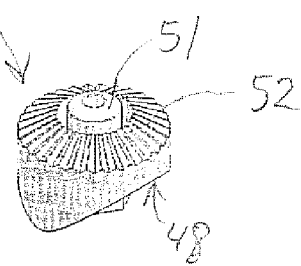

ADJUSTABLE SUPPORT

ADJUSTABLE SUPPORT

This application claims the benefit of Danish Application No. PA 2009 00872 filed Jul. 16, 2009 and PCT/DK2010/050172 filed Jun. 29, 2010, International Publication No. WO 2011/006502 A1, which are hereby incorporated by reference in their entirety as if fully set forth herein.

FIELD OF THE INVENTION

The present invention concerns an adjustable support, particularly in relation to human necessities. The invention also concerns a segment forming part of the adjustable support and a supporting surface as well as uses of the adjustable support.

BACKGROUND OF THE INVENTION

When caring for disabled persons or patients in a hospital ward, there is often use for various kinds of adjustable supports for headrests, seat backs, mattresses and similar uses. Also, adjustable supports are often applied in connection with equipment, e.g. lamp stands, especially on tables, tool holders and brackets for various applications, where adjustability is required for proper function or for convenience.

U.S. Pat. No. 6,758,808 discloses an adjustable support or stabilisation device including an elongated structure consisting of segments engaging each other in succession. Each segment is provided with opposed pivot surfaces at respective ends thereof, facing away from each other for contacting and abutting on an adjacent segment. The two opposed pivot surfaces of each segment are provided with complementing convex and concave, respectively, curving shapes that are generally partially cylindric and provided with teeth-like projections. The support is held in fixed position by means of a tensioning wire extending through the segments in the elongated structure as the teeth-like projections on abutting segments engage each other. The support of this U.S. patent is designed as an arm or bracket for stabilising tissue to perform surgery while the heart of the patient continues to beat. The mutually engaging teeth-like projections of the segments of the support extend along the curvature of the complementing pivot surfaces so as to guide the segments in their pivoting movement. Since the teeth-like projections extend along the curvature of the pivot surfaces, there is only friction to hold the support in fixed shape and position. Consequently, it is limited how great a load the support can carry or resist in use.

Due to the special application, the segments in the support of U.S. Pat. No. 6,758,808 are largest and widest at the base, becoming successively smaller towards the distal end. In production, this requires special moulds or manufacturing for each segment, depending on the position of the individual segment in the succession. Also, the segments and support according to this prior art are only adjustable in one plane due to the design of the segments and their pivot surfaces.

A further example of an adjustable support structure is disclosed in EP 2039271. In this construction, alternating circle cylindrical elements and substantially rectangular elements are assembled, in order to provide flexibility as to the shape of the structure. When being assembled, tightening of through going wires, the alternating circle cylindrical elements and substantially rectangular elements are locked mutually, allowing the elements to be mutually fixed, such that the assembled plurality of circle cylindrical elements and substantially rectangular elements represents the shape of a curve or the like. The structure according to EP2039271 therefore relies on at least two different elements in order to assemble a support. When branches or the like needs to be added further special elements, not disclosed, shall be used.

OBJECT OF THE INVENTION

One object of the invention is to provide an adjustable support of the kind mentioned in the introduction for universal use where easy and frequent adjustment is possible. A further object of the invention is to provide a segmented adjustable support of the kind mentioned in the introduction that can carry a greater load than the prior art support combined with great flexibility in adjustment.

DESCRIPTION OF THE INVENTION

According to the invention, this is achieved by an adjustable support of the kind specified in the preamble of claim 1 and a segment for such a support as specified in the preamble of claim 6 which are peculiar in that the teeth-like projections extend in parallel with generatrices to the partially cylindric shape of the opposing pivot surfaces.

Compared with the prior art, the teeth-like projections of the segment according to the invention extend transversely of the curving pivot surfaces instead of along these faces. A far greater stability is thus provided in the adjustable support since the retention force is not only provided by friction between the abutting surfaces of adjacent segments but also by the bending moment being resisted by the interacting teeth-like projections.

The support according to the invention is preferably designed such that respective ends of the segment are provided with separate complementing guideways, respectively, that largely follow the curvature of the pivot surface. Lateral sliding between abutting segments is thus impeded. An enhanced effect in this respect is achieved if the guideways on a segment are formed as recesses and projections, respectively.

In a preferred embodiment of the invention, the support and the segment according to the invention are designed such that each segment is divided transversely to the centre axis of the through-going hole into two parts, the interface between the parts designed such that the parts may rotate in relation to each other about an axis in the through-going hole and such that the parts can be fixed, preventing mutual rotation when a force is applied to the segment along the axis. As each segment is thus provided freedom of rotation about a central axis passing in longitudinal direction of the support, a far greater adjustability is provided of the adjustable support. Adjusting the support in more than one plane, i.e. in three dimensions, is thus possible.

A practical embodiment of the segments has the feature that the interface between the parts includes a central tubular projection on one part and a complementing socket on the other part, and wherein abutting faces in the interface is provided with radially extending surface structure, e.g. knurls or teeth.

The invention also provides for an adjustable surface for supporting a person which includes at least two adjustable supports arranged substantially in parallel directions. An adjustable mattress or bed may thus be designed with several parallel supports according to the invention. When the wire is loosened, the bed or mattress can be formed according to the physiognomy of the person lying thereon. Similar applications are possible with seats, seat backs, leg supports etc., whether in connection with common chairs or wheelchairs.

The inventive adjustable support can be used as support for a headrest, particularly a headrest for a disabled person.

It is preferred to make the basic segments of the adjustable support according to the invention identical, thus minimising the manufacturing cost and providing a modular unit that can be used in very different supports.

DESCRIPTION OF THE DRAWING

Preferred embodiments of the invention will be described below with reference to the drawings, on which:

FIG. 1 shows a perspective view of an embodiment of an adjustable support according to the invention in the form of a headrest;

FIG. 2 shows the support of FIG. 1, seen in a view from above;

FIG. 3 shows a section on the line III-III on FIG. 2;

FIGS. 4a-b show bottom and top perspective views, respectively, of a first part of an embodiment of a segment according to the invention;

FIGS. 5a-c show a bottom and two side views, respectively, of the part on FIGS. 4a-b;

FIGS. 6a-b show bottom and top perspective views, respectively, of a second part of an embodiment of a segment according to the invention;

FIGS. 7a-c show bottom and two side views, respectively, of the part on FIGS. 6a-b;

FIGS. 8a-b show a side and a front views, respectively, of a branch member for use in the adjustable support in FIG. 1;

FIG. 9 shows a section on the line IX-IX on FIG. 8b;

FIG. 10 shows an enlarged detail of the support on FIG. 1;

FIG. 11 shows the same as FIG. 10, but fitted with extension adapters;

FIGS. 12a-b show two perspective views of a first extension adapter; and

FIGS. 13a-b show two perspective views of a second extension adapter.

DETAILED DESCRIPTION OF EXAMPLE EMBODIMENTS

The adjustable support according to the invention is exemplified by an embodiment in the form of a headrest particularly designed for use on wheelchairs and chairs for disabled as well as for use in treatment, e.g. dentists' chairs.

The headrest shown on FIGS. 1-3 comprises a bar 1 for mounting, e.g. inserting in a socket, on the top of a seat back, an adjustable segmented arm 2 and an adjustable segmented head support 3. The joint between the arm 2 and the head support 3 is comprised by a branch member 4 designed to received adjoining segments 20 and 30, respectively, of the arm 2 and the head support 3.

The uniform arm segments 20 are held together by a through-going wire 5. The wire 5 is joined with the top end of the bar 1 by a tightening mechanism 6 in that the lower end of the wire 5 is secured to a hexagonal piece 7 slidably, but non-rotatably received in a hole provided by the mechanism 6, see FIG. 3. The piece 7 is provided a not shown internal thread facing away from the wire. A screw 8 is arranged fixed inside a rotatable operating knob 9 seated around a tubular formation 10 extending from the bar 1 such that turning the knob 9 will turn the screw 8. The other end of the wire 5 is fixed in the branch member 4 by a pointed screw 11 in a cylindric or hexagonal element 12. The arrangement thus causes the wire 5 to be tightened or loosened by sliding movement of the piece 7, depending on the direction of rotation of the knob 9 and the screw 8. In the loose state, the individual segments 20 may thus move in relation to each other, thus making adjusting the shape and direction of the arm 2 possible. In the tightened state, the segments 20 are held firmly together, fixing the shape of the arm 2 and enabling the arm 2 to support and carry a substantial load.

Since the segments 20 are identical, a modular design is achieved, making production cheap and enabling a great variety of embodiments of the support according to the invention, depending on the application The head support segments 30 are joined in a corresponding, but not shown way to the branch member 4. The segments 30 are similar to the segments 20 except for rigid, oppositely directed tabs 31 provided for forming attachment means for padding of the head support or similar. The two branches 3a of the head support 3 each end with a rotatable operating knob 9 similar to that provided for the arm 2. Adjusting the branches 3a is effected in the same way as with the arm 2.

Each segment 20 is largely cylindric in shape, displaying curving first and second ends 21, 22, respectively. The segment 20 is provided with a central, through-going hole 23 for accommodating wire 5, and the segment 20 is divided transversely, preferably perpendicularly, to the centre axis of the hole 23 into a first part 20a and a second part 20b.

The interface between the parts 20a, 20b is provided with aligning means in the form of a cylindric sleeve 24 on the first part 20a and a cylindric stub 25 on the second part 20b. The stub 25 engages the sleeve 24 so as to centre and secure the parts 20a, 20b against lateral displacement.

The interface between the parts 20a, 20b is furthermore provided with teething 26 disposed at the rim of the abutting sides of the parts 20a, 20b such that the teeth 26 extend radially from the centre axis of the segment 20. The teething 26 is shown concave and convex, respectively, on the parts 20a, 20b, but this is not essential for the invention. When tightening the wire 5 and thus squeezing the parts 20a, 20b together, the teeth 26 will by mutual engagement provide resistance against mutual rotation of the parts 20a, 20b, while loosening the wire 5 will allow for mutual rotation of the parts 20a, 20b and thereby rotational adjustment of the arm 2.

The first end 21 on each segment 20 provided on the part 20a has a partially cylindric, concave area 27 which is provided with teething or a similar jagged formation extending in parallel with a generatrix for the area 27. At each side of the area 27 is provided recessed guides 18 having a curvature that follows the curvature of the area 27.

The second end 22 of each segment provided on the part 20b has a complementing convex, partially cylindric area 29 provided with teething or a similar jagged formation extending in parallel with a generatrix for the area 29. At each side of the area 27 is provided projecting guides 19 that are complementary to the recessed guides 18 so as to guide abutting ends 21, 22 of adjacent segments 20 when the segments perform a pivoting movement during adjustment of the arm 2.

With regard to details pertaining to design and mutual interaction, the segments 30 are identical with the segments 20, i.e. a two-part construction with specially designed engagement faces for securing the arm 3 in a desired configuration.

The adjustable support according to the invention may be adapted in many ways according to the applications thereof, of which the described headrest is only one such. Special members or segments can be designed for adapting the adjustable support to the particular use. In the present example, this includes a branch member 4 providing a bifurcation into two branches 3a.

The branch member 4, see FIGS. 8a-b and 9, connects the arm 2 and the branches 3a at three sides 41 which are all configured like the second end 22 of part 20b of the segment 20. This means that the first end 21 of a segment 20 as well as first ends of similar segments 30 may be joined to the member 4 and held by a wire 5. The wire going through the branches 3a is not shown but may expediently be continuous through the member 4 through a hole 42 and fastened at each end to adjusting mechanisms provided by knobs 9 at the free ends of branches 3a. The socket 44 between the tabs 31 is provided for accommodating an element 12 for fastening the end of the wire 5.

Sockets 43 are provided for extending the adjustable support transversely to the general orientation of the branch member 4, e.g. for connecting to similar adjustable supports or arms or for other purposes, e.g. mounting auxiliary equipment or nonadjustable supporting devices. The sockets 43 are here provided oppositely disposed on the member 4, but otherwise identical. They 43 are provided with hexagonal bottom for rotationally fixing extension adapters 45 and 46, see FIGS. 11, 12a-b and 13a-b. Both extension adapters 45, 46 are provided with hexagonal stubs 47 for engaging the bottom of sockets 43 and are also provided with curving contact faces 48 around the stubs 47 for fitting closely to the outer curvature of the cylindric surface of the branch member 4.

Opposite the stub 47 on the first extension adapter 45 there is provided an interface which in principle is similar to that of the first part 20a of segment 20, i.e. with a central cylindric sleeve 49 and surrounding concave teething 50. This interface may then be connected with a second part 20b of a segment 20, thus enabling continuation of an arm 2 or a branch 3a in transverse direction from the member 4.

The second extension adapter 46 is similarly configured as the second part 20b of the segment 20, i.e. with a central cylindric stub 51 and surrounding convex teething 52. This interface may then be connected with a first part 20a of a segment 20, thus enabling continuation of an arm 2 or a branch 3a in transverse direction from the member 4. Interconnection between two branch members 4 arranged in parallel is obviously also possible in this way.

The headrest thus provided may be adjusted in several dimensions, including by rotating the arms 2 and 3 about their axes and bending, including S-shaped bends.

The adjustable support according to the invention may be applied in many other ways. For example, lamp stands, tool holders and bracket-like devices may easily be provided great flexibility by the invention, while still being able to support or withstand larger loads than prior art supports that depend on friction only for fixing their shape. Also, a support according to the invention may be designed as a support surface which is covered by a padding or flexible surface in that several arms like the embodiments 2 or 3 are arranged in parallel and possibly interconnected transversely. Such an adjustable surface may be usable for beds for patients or disabled persons.

The invention claimed is:

1. Adjustable support including an elongated structure consisting of segments engaging each other in succession, wherein each segment is provided with opposed pivot surfaces at respective ends thereof, facing away from each other for contacting and abutting on an adjacent segment, the two opposed pivot surfaces of each segment being provided with complementing convex and concave, respectively, curving shapes that are generally partially cylindric and provided with teeth-like projections, and wherein the support is held in fixed position by means of a wire extending through the segments in the elongated structure as the teeth-like projections on abutting segments engage each other, wherein the teeth-like projections extend in parallel with generatrices to the partially cylindric shape of the opposing pivot surfaces, and where each segment consists of two parts, a first part and a second part, where an adjustable interface is provided between said first and second parts.

2. The adjustable support according to claim 1, wherein respective ends of the segment are provided with separate complementing guideways, respectively, that largely follow the curvature of the pivot surface.

3. The adjustable support according to claim 2, wherein the guideways on a segment are formed as recesses and projections, respectively.

4. The adjustable support according to claim 1, wherein each segment is divided transversely to the centre axis of the through-going hole into said first and second parts, the interface between said parts designed such that said parts may rotate in relation to each other about an axis such that the parts can be fixed, preventing mutual rotation when a force is applied to the segment along the axis.

5. The adjustable support according to claim 4, wherein a through going hole is provided about said axis through each segment.

6. The adjustable support according to claim 4, wherein the interface between said parts includes a central tubular projection on one part and a complementing socket on the other part, and wherein abutting faces in the interface is provided with radially extending surface structure, e.g. knurls or teeth.

7. A segment for an adjustable support according to claim 1, the segment adapted for forming part of an elongated structure, wherein the segment is provided with opposing pivot surfaces for contacting and abutting on another adjacent segment, the two pivot surfaces of the segment being provided with complementing curving shapes that are generally partially cylindric and provided with teeth-like projections, and wherein the segment is provided with a through-going hole for a wire opening in the opposing surfaces, wherein the teeth-like projections extend in parallel with generatrices to the partially cylindric shape of the opposing pivot surfaces and where each segment consists of two parts, a first part and a second part, where an adjustable interface is provided between said first and second parts.

8. The segment according to claim 7, wherein the segment is divided transversely to the centre axis of the through-going hole into said two parts, the interface between said parts being designed such that the parts may rotate in relation to each other about an axis in the through-going hole and such that the parts can be fixed, preventing mutual rotation when a force is applied to the segment along said axis.

9. The segment according to claim 8, wherein the interface between said parts includes a central tubular projection on one part and a complementing socket on the other part, and wherein abutting faces in the interface is provided with radially extending surface structure, e.g. knurls or teeth.

10. An adjustable surface for supporting a person, including at least two adjustable supports according to claim 1 arranged substantially extending in parallel directions.

11. Use of an adjustable support according to claim 1 as support for a headrest, particularly a headrest for a disabled person.

12. Use of an adjustable support according to claim 1 for a bed or a mattress.

* * * * *